(12) United States Patent
Booker

(10) Patent No.: US 7,174,767 B2
(45) Date of Patent: Feb. 13, 2007

(54) PARTICULATE MATTER ANALYZER AND METHOD OF ANALYSIS

(75) Inventor: David R. Booker, Wantage (GB)

(73) Assignee: Sensors, Inc., Saline, MI (US)

( * ) Notice: Subject to any disclaimer, the term of this patent is extended or adjusted under 35 U.S.C. 154(b) by 78 days.

(21) Appl. No.: 11/001,325

(22) Filed: Dec. 1, 2004

(65) Prior Publication Data
US 2005/0160792 A1 Jul. 28, 2005

Related U.S. Application Data

(60) Provisional application No. 60/525,990, filed on Dec. 1, 2003.

(51) Int. Cl.
*G01N 29/02* (2006.01)
(52) U.S. Cl. .................... 73/24.01; 73/31.03; 73/28.02
(58) Field of Classification Search .............. 73/24.01, 73/24.03, 24.06, 28.02, 31.03
See application file for complete search history.

(56) References Cited

U.S. PATENT DOCUMENTS 5,349,844 A * 9/1994 Lilienfeld .................. 73/28.01
5,892,141 A * 4/1999 Jones et al. ................ 73/24.03
6,510,727 B2 * 1/2003 Reiter et al. ............... 73/24.03
6,786,075 B2 * 9/2004 Radke et al. ............... 73/24.06
6,972,841 B2 * 12/2005 Krempl et al. .............. 356/338

FOREIGN PATENT DOCUMENTS

GB 2371362 A * 7/2002

OTHER PUBLICATIONS

J. E. Brockmann et al. "A Sample Extraction Diluter for Ultrafine Aerosol Sampling" Aerosol Science and Technology, 1984, 441-451.*

* cited by examiner

*Primary Examiner*—Michael Cygan
(74) *Attorney, Agent, or Firm*—Van Dyke, Gardner, Linn & Burkhart, LLP

(57) ABSTRACT

An apparatus and method for the analysis of particles in an aerosol includes providing an inlet for the aerosol, a sample collector which accumulates particles passing through the inlet, a sample conditioning system which can vary at least one condition relating to the collected sample, a controller which causes the sample conditioning system to operate at select conditions, a measuring device for determining at least one parameter relating to the accumulated particles. The controller monitors the parameter while the condition is varied.

4 Claims, 4 Drawing Sheets

PARTICULATE MATTER ANALYZER AND METHOD OF ANALYSIS

CROSS REFERENCE TO RELATED APPLICATION

This application claims priority from U.S. provisional patent application Ser. No. 60/525,990, filed on Dec. 1, 2003, the disclosure of which is hereby incorporated herein by reference in its entirety.

BACKGROUND OF THE INVENTION

This invention relates to an apparatus and a method of analysis for differentiating between different types of particulate matter.

During monitoring of air quality, and/or vehicle emissions, aerosol particulate matter may be collected on for example the piezo-electric crystal sensor of a mass sensitive microbalance by use of an electrostatic precipitator. A known microbalance is described in "Piezoelectostatic Aerosol Mass Concentration Monitor," by Olin J G, Sem G J & Christenson D L, Amer. Ind. Hyg. Assoc. J 32: 209 (1970). Particulate matter is collected on the sensor which records the weight of material collected. A problem with this type of analyzer is that it fails to distinguish between volatile and non-volatile particulate matter collected on the sensor. Volatile particulate matter may evaporate from the sensor over a longer or shorter time period, and different particles collected may be reactive, resulting in mass change on the sensor. Even real time microbalances have to be calibrated using non volatile particles.

For an air quality assessment, this problem is presently addressed by using an agreed factor determined by the EC Working Group on Particulate Matter to convert monitored readings into EU standard gravimetric readings. This factor has recently been set at 1.3, but trials have indicated that the factor varies between 1.0 and 1.6 depending upon the location of the monitor season.

Other particle analysis systems collect particles on a filter which is then weighed. This again cannot give any accurate indication of the mass of lost volatile particulates, or mass changes associated with chemical reactions occurring in the filtrate.

The present invention seeks to provide an improved analyzer and method of analysis for aerosols which gives a more accurate indication of the volatile particle content of the total particulate matter in the aerosol and the reactivity of the collected particles to both water absorption and chemical reaction.

STATEMENTS OF INVENTION

According to the present invention, there is provided apparatus for the analysis of particles in an aerosol and which includes an inlet for the aerosol, a sample collector which accumulates particles passing through the inlet, a sample conditioning system which can vary at least one condition relating to the collected sample, a controller which causes the sample conditioning system to operate at select conditions, a measuring device for determining at least one parameter relating to the accumulated particles, and monitoring means monitoring said parameter whilst said condition is varied.

Preferably, the sample collector is an electrostatic precipitator. The measuring device may comprise a device for measuring optical properties of the sample, e.g., light scatter, or preferably a mass sensor such as a microbalance, e.g., a piezoelectric quartz crystal.

The sample conditioning system may control at least one of humidity, temperature, and more preferably sample dilution. The dilution means dilutes the aerosol with clean filtered air and is variable to produce different dilution ratios. The controller controls the dilution means to operate at selected dilution ratios for selected time periods. Preferably, the monitoring means monitors the mass of collected particles on the sensor over a selected time period at different dilution ratios.

According to a further aspect of the invention, there is provided a method of analysis of the particulate content of an aerosol, and which comprises passing reference aerosols of known content, singly, over a sample collector which accumulates particles from said aerosol, measuring at least one parameter relating to the respective collected sample of particles, varying at least one condition relating to aerosol sample collection, and monitoring said parameter for the select conditions as said conditions are varied, producing data relating to said parameter, storing said data, then passing an aerosol of unknown particulate content and measuring said parameter for said varying conditions to produce the respective data, and deconvoluting said data against previously stored data using a multivariable non-linear optimization algorithm to produce information relating to the content of the unknown particulate content.

Preferably, the particles are collected by precipitation and are collected on a mass sensor for measuring of the weight of particles on the mass sensor versus elapsed time.

The sample aerosol may be diluted at different dilution ratios with clean gas or air and the mass measured as the dilution ration is varied say between 1 and 10 or 1 and 2. The dilution may be varied in regular cycles or non-cyclically whichever is preferred.

At any particular time, the mass on the collecting surface is given by:

$$Mt = Mv + Mnv - Me$$

Where:
  Mt is the total mass of particulates,
  Mv is the mass of volatile particles,
  Mnv is the mass of non-volatile particles, and
  Me is the mass of evaporated volatiles, which may be due to physical and chemical reactions.

Additional terms reflecting changes due to chemical reactivity and to the absorption of gases can also be added to the above equation.

Since for any combination of particle concentration, and % volatile present there is only one solution to the deconvoluted data, it is possible to analyze the aerosol for the percentage of volatile matter present and the original concentration of particulate matter present.

DESCRIPTION OF THE DRAWINGS

The invention will be described by way of example and with reference to the accompanying drawings in which.

DETAILED DESCRIPTION OF THE INVENTION

Figure 1:
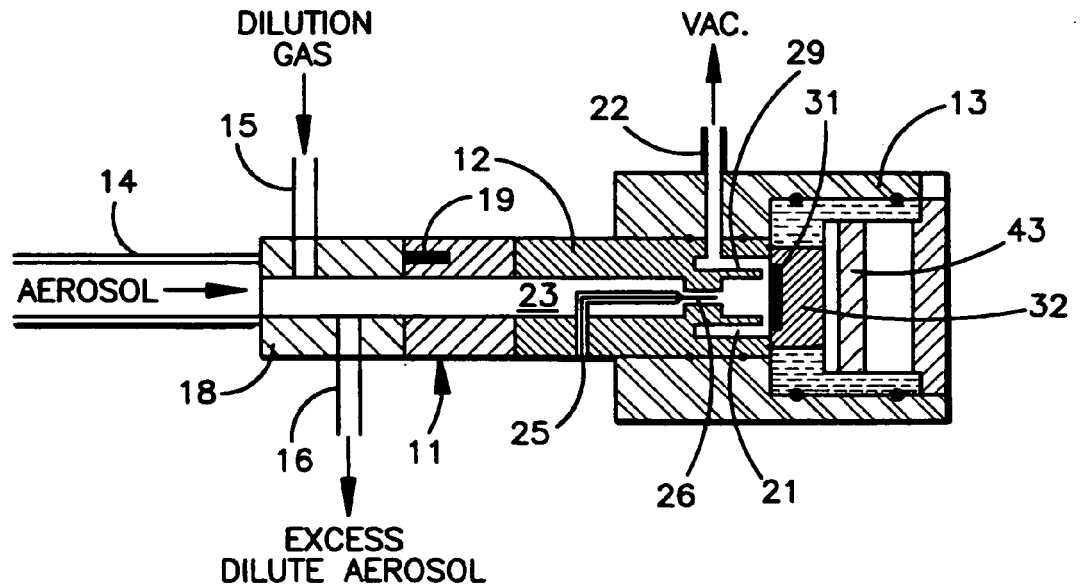
FIG. 1 is a schematic section through apparatus according to the present invention.
Figure 2:
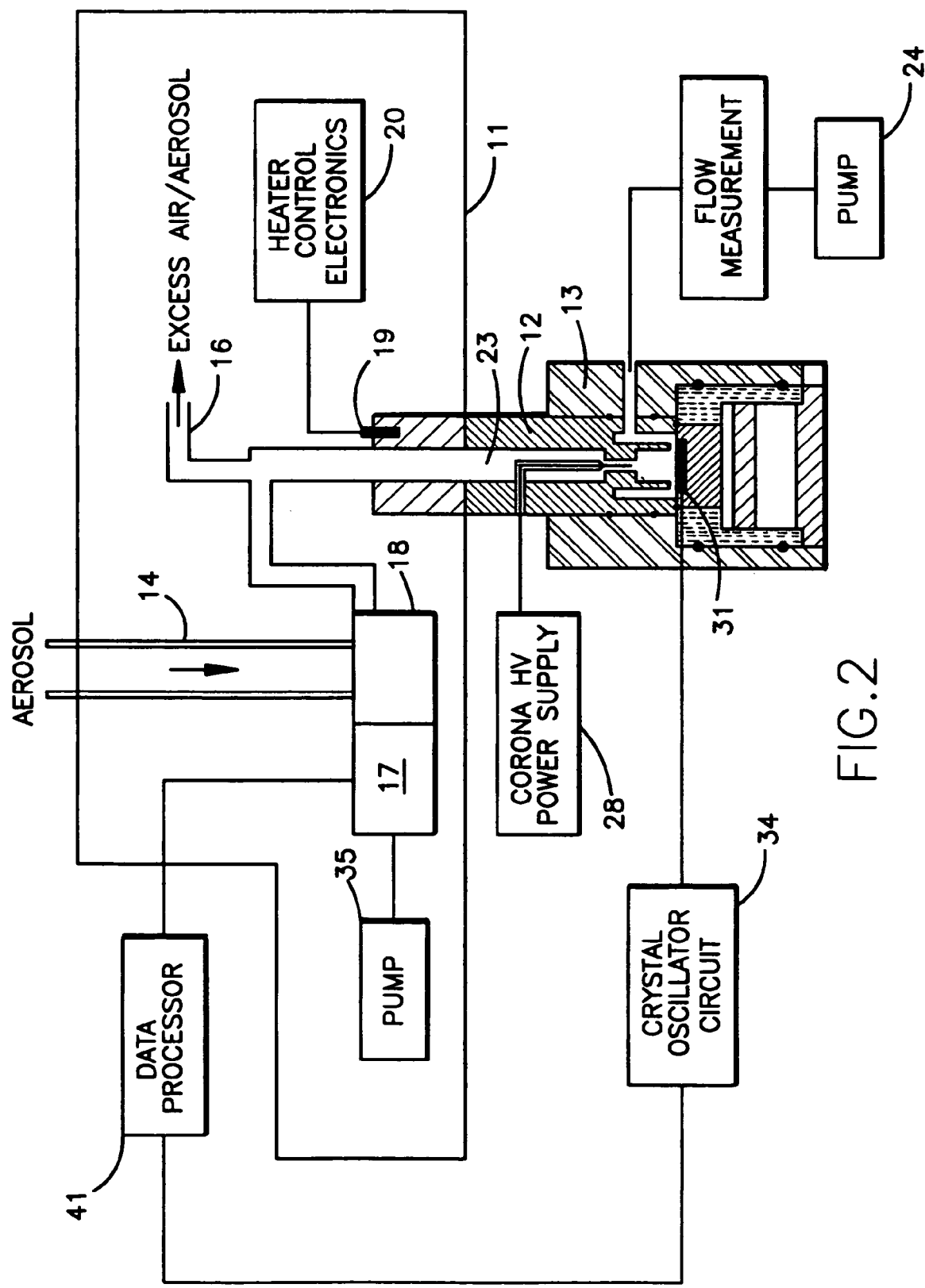
FIG. 2 is a schematic drawing of the control system of the apparatus of FIG. 1.

With reference to FIG. 1 and FIG. 2, there is shown an aerosol analyzer 10 which comprises a sample conditioner 11, an electrostatic precipitator 12, and a mass microbalance 13.

The sample conditioner 11, includes an aerosol diluter 18 and heater 19 and may also include a humidifier. The conditioner 11 has an inlet 14 which receives the aerosol and a dilution gas input 15 and an outlet 16 for a mixture of excess dilution gas and aerosol. The dilution gas is typically clean air, but could be other gases. The diluter 11 operates to dilute the aerosol sample entering the precipitator 12. The precipitator 12 and mass microbalance 13 operate on a substantially steady airflow, e.g., 2 litre per minute. Any aerosol entering the inlet 14 may be diluted by a known dilution ratio so that the steady flow to the microbalance is maintained and excess aerosol/gas mixture is dumped to atmosphere. A known diluter 18 is disclosed in "A Sample Extraction Diluter for Ultrafine Aerosol Sampling," by J. E. Brockman, B. Y. H. Liu, and P. H. McMurray Aerosol Science & Technology, 441–451 (1984), and a suitable instrument is available from Booker Systems, England under the name Booker Systems, SCS. The dilution air is drawn in by a pump 35 and the dilution ratio of the aerosol sample passing into the precipitator 12 is controlled by a programmable controller 17.

The heater 19 is controlled by a heater control 20 so that the aerosol temperature may be varied as is desired.

The conditioned aerosol passes into a particle charging chamber 23 within the precipitator 12. A corona needle 26 is located within the chamber 23 and is connected to a high voltage power supply 28 via electrical conductors 25. The precipitator body is typically made from an electrically insulating material and makes a gas-tight seal with the mass microbalance 13. The inner end of the precipitator has a hollow spigot 29 which is connected to the chamber 13 and which in use directs the charged aerosol flow onto a mass sensor 31 in the balance 13. The spigot 29 is surround by an annular cavity 21 which is connected to a radial port 22 through which the conditioned aerosol exits the precipitator via a vacuum pump 24.

The precipitator 12 is located in the body of the microbalance 13 so that it is aligned with the mass sensor 31, preferably a piezoelectric quartz crystal sensor of a type described in U.S. Pat. No. 3,653,253. The sensor 31 is mounted in a holder 32 located in the body. As particles pass the needle 26, they pick up a charge from the intense ion field near the needle tip and are driven towards the collection surface on the sensor 31. The quartz crystal sensor 31 is preferably in the form of a disc which can be removed from the holder 32 for cleaning, storage, etc. Electronic controls 34 for the crystal sensor may be located in the microbalance 13 and include an oscillator, to drive and measure crystal frequencies, and a heater control for control of the crystal temperature.

Figure 3:
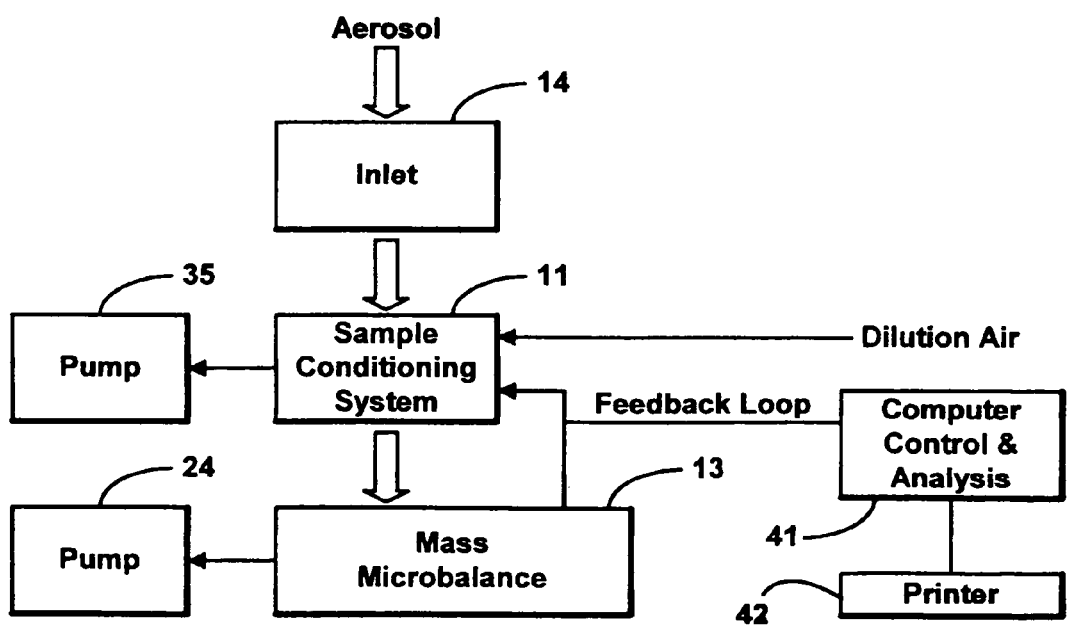
FIG. 3 is a flowchart showing the method according to the present invention.

With reference also to FIG. 3, in use the aerosol is drawn into the analyzer 10 through inlet 14 by the vacuum pump 24 which draws the aerosol through the chamber 23 of the microbalance 13. Before entering the precipitator 12, the aerosol passes through the sample conditioning system 11.

The sample conditioning system can operate to vary at least one condition of the aerosol sample, for example, its temperature, humidity or preferably its dilution factor. The dilution control 17 can be operated to vary the dilution factor in a desired way over a desired time cycle. A main computer control/processor 41 is connected to the microbalance control 34 and the dilution control 17 to monitor the mass of collected particles and dilution factor versus elapsed time. The main control 41 may be connected to a printer 42 to produce printouts as shown in FIGS. 4 and 5.

Figure 4:
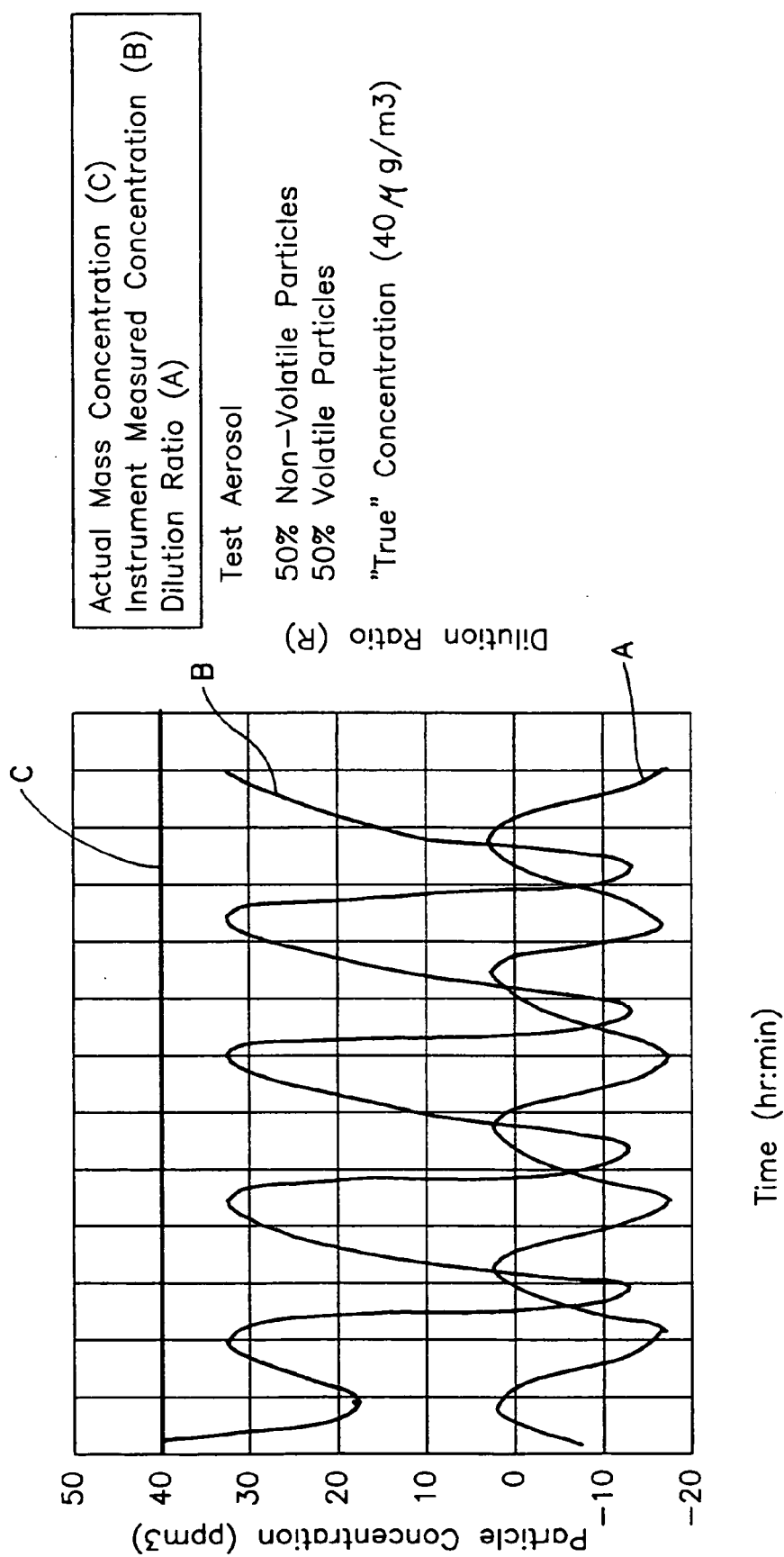
FIG. 4 is a graph of measured mass and dilution ratio versus elapsed time for a first aerosol sample.

For example, and with reference to FIG. 4, the dilution ratio R for a particular aerosol concentration containing 50% non-volatile particles and 50% volatile particles may be altered sinusoidally between 1 and 10 over a 12-minute cycle time (Curve A) during which time the particle mass on the sensor is measured (Curve B). The total actual concentration of particle is given by the line C. It should be noted that initially the measured aerosol particle concentration is close to the true concentration and it then cycles between $-15$ and $30$ $\mu g/m^3$. As dilution increases, the relative importance of the loss of volatile particles versus new particles being collected, shifts in favor of the volatile component.

Figure 5:
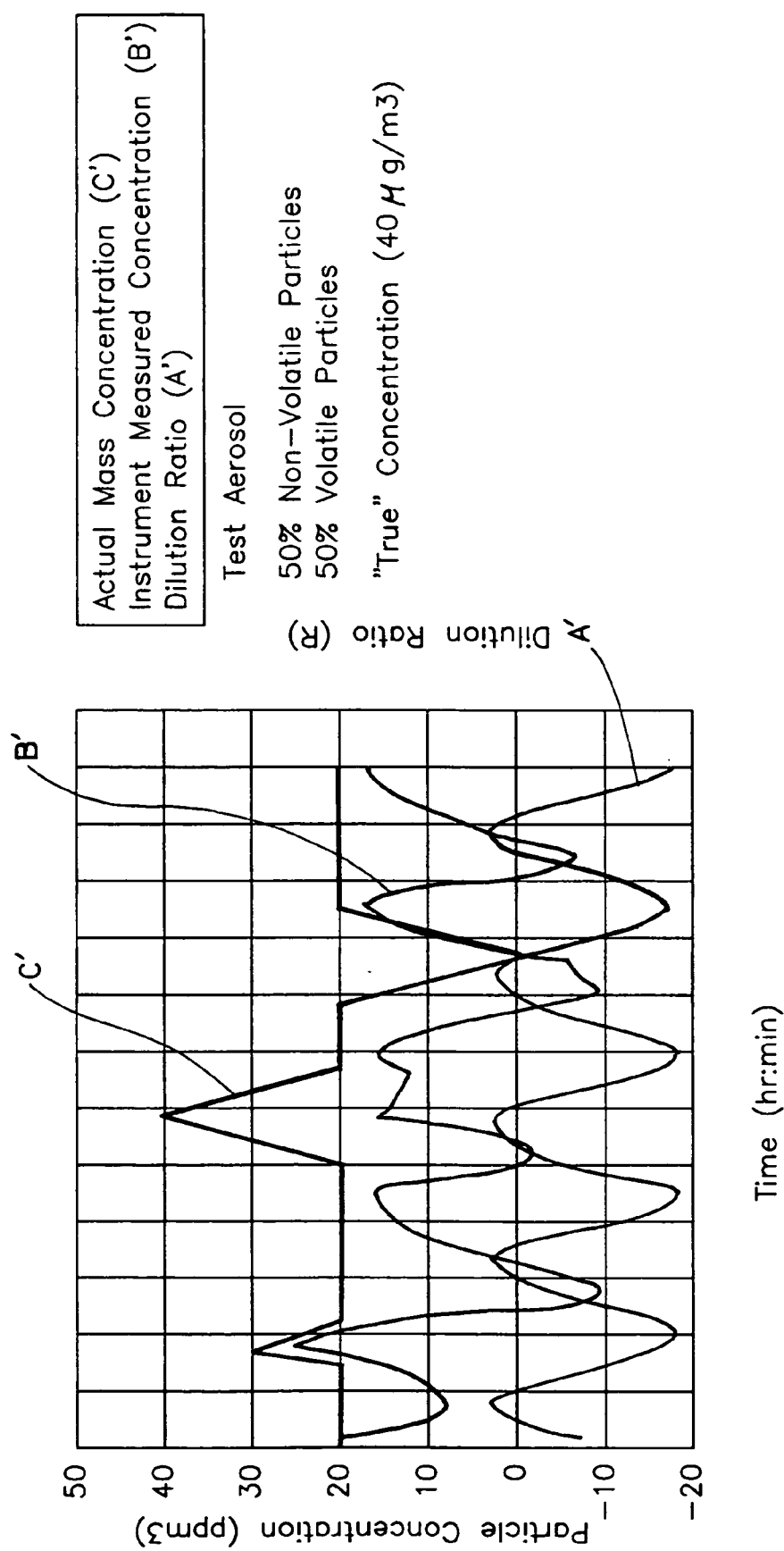
FIG. 5 is a graph of measured mass and dilution ratio versus elapsed time for a second aerosol sample.

If the sampled aerosol does not contain a constant particle concentration, then for the same 50:50 mix of non-volatile: volatile particles, then the curves A', B' and C' may be obtained, as shown in FIG. 5.

Although not essential for the determination of the aerosol characteristics, different data is initially obtained for known ratio mixes of non-volatile:volatile particles at particular particle concentrations. In particular, for mixes with non-volatiles contents of 90%, 50% and 70%, so that the main computer control 41 builds up a stored knowledge of the different curves B for different ratio mixes, different concentrations and different dilution ratio cycles. The control is programmed to solve for the aerosol characteristics by using a multivariable non-linear optimization algorithm. The above data sets provide starting conditions for deconvolution.

When an unknown aerosol sample is analyzed, the computer searches its stored data and matches the information obtained from the unknown sample to the data in its stored memory to solve for the optimum match. Since each match is unique for a particular particle concentration and particular % volatile content an analysis of the sample can be produced in those terms.

The dilution ration may be altered in other cyclic patterns or in a cyclic manner and other sample conditions may be varied alternatively or additionally, for example the temperature, and/or humidity of the aerosol.

The invention claimed is:

1. A method of analysis of the particulate content of an aerosol, comprising:
    passing reference aerosols of known content over a sample collector which accumulates particles from said aerosol;
    measuring at least one parameter relating to the respective collected sample of particals;
    varying at least one condition relating to the respective aerosol sample;
    monitoring said parameter for the select conditions as said conditions are varied, producing data for said respective aerosol sample relating to said parameter, storing said data;
    passing an aerosol of unknown particulate content and measuring said parameter for said varying conditions to produce the respective data, wherein said condition is varied cyclically with respect to time and deconvoluting said data against previously stored data using a multivariable non-linear optimization algorithm to produce information relating to the content of the unknown particulate content;

collecting the particles by precipitation and with a mass sensor for measuring of the weight of collected particles on the mass sensor versus clansed time; and diluting the sample aerosol at different dilution ratios with clean gas or air, wherein the dilution ratio is varied between 1 and 10.

2. A method as claimed in claim 1, wherein the dilution ratio is caused to vary in regular cycles, preferably sinusoidally.

3. A method of analysis of the particulate content of an aerosol, comprising:

passing reference aerosol of known content over a sample collector which accumulates particles from said aerosol;

measuring at least one parameter relating to the respective collected sample of particles;

varying at least one condition relating to the rspective aerosol sample;

monitoring said parameter for the select conditions as said conditions are varied, producing data for said respective aerosol sample relating to said parameter, storing said data;

passing an aerosol of unknown particulate content and measuring said parameter for said varying conditions to produce the respective data, and deconvoluting said data against previously stored data using a multivariable non-linear optimization algorithm to produce information relating to the content of the unknown particulare content; and diluting the sample aerosol is diluted at different dilution ratios with clean gas or air, wherein the dilution ratio is varied between 1 and 10.

4. A method as claimed in claim 3, wherein the dilution ratio is caused to vary in regular cycles, preferably sinusoidally.

* * * * *

UNITED STATES PATENT AND TRADEMARK OFFICE
CERTIFICATE OF CORRECTION

PATENT NO. : 7,174,767 B2  Page 1 of 1
APPLICATION NO. : 11/001325
DATED : February 13, 2007
INVENTOR(S) : David R. Booker It is certified that error appears in the above-identified patent and that said Letters Patent is hereby corrected as shown below:

Column 4:
Line 57, Claim 1, "particals" should be --particles--.

Column 5:
Line 7, Claim 1, "clansed" should be --elasped--.
Line 16, Claim 3, "aerosol" should be --aerosols--.
Line 21, Claim 3, "rspective" should be --respective--.

Column 6:
Line 11, Claim 3, "particulare" should be --particulate--.

Signed and Sealed this

Twenty-eighth Day of August, 2007

JON W. DUDAS
*Director of the United States Patent and Trademark Office*